(12) United States Patent
Franze et al.

(10) Patent No.: US 6,673,575 B1
(45) Date of Patent: Jan. 6, 2004

(54) METHOD FOR PREPARING POLYPEPTIDES WITH APPROPRIATE GLYCOSILATION

(75) Inventors: Reinhard Franze, Penzberg (DE); Horst Eberhardt, Penzberg (DE); Claus Wallerius, Penzberg (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/555,533

(22) PCT Filed: Dec. 2, 1998

(86) PCT No.: PCT/EP98/07819

§ 371 (c)(1), (2), (4) Date: Sep. 5, 2000

(87) PCT Pub. No.: WO99/28455

PCT Pub. Date: Jun. 10, 1999

(30) Foreign Application Priority Data

Dec. 3, 1997 (DE) .......................... 197 53 681
Jul. 17, 1998 (EP) ............................ 98113409

(51) Int. Cl.[7] .............................. C12P 21/00; C12N 5/00
(52) U.S. Cl. ..................... 435/71.1; 435/348; 435/325; 435/373
(58) Field of Search ................................. 435/404, 405, 435/406, 68.1, 70.1, 70.3, 71.1, 348, 325, 326, 69.4, 373; 514/8

(56) References Cited

U.S. PATENT DOCUMENTS

| | | | |
|---|---|---|---|
| 4,935,350 A | | 6/1990 | Avanika et al. |
| 5,705,364 A | * | 1/1998 | Etcheverry et al. |
| 5,856,298 A | * | 1/1999 | Strickland |

FOREIGN PATENT DOCUMENTS

| | | |
|---|---|---|
| EP | 0 550 756 A1 | 7/1993 |
| JP | Hei 04-281797 | 10/1992 |
| JP | Hei 06-292592 | 10/1994 |
| WO | WO 92/18537 | 10/1992 |

OTHER PUBLICATIONS

Yoda et al., "Time Course of Glutamine in a Culture Medium during High–Density Culture of Mouse C127 Transformants," Annals New York Academy of Sciences, 1995, p. 176–179.*

Ljunggren et al., "Catabolic Control of Hybridoma Cells by Glucose and Glutamine Limited Fed Batch Cultures," Biotechnology and Bioengineering, vol. 44, 1994, p. 808–818.*

Database WPI, Section Ch, Week 9502, Derwent Publications Ltd., AN 95–009082.

Yoda et al., Annals of the New York Academy of Sciences, 750:175–179 (1995).

Panneerselvam et al. The Journal of Biological Chemistry, 272:23123–23129 (1997).

Ljunggren, Biotechnology and Bioengineering, 44:7:808–818 (1994).

Andersen, Current Opinion in Biotechnology, 5:546–549 (1994).

Takeuchi et al., Proceedings of the National Academy of Sciences of USA, 86:7819–7822 (1989).

Xie, Trends in Biotechnology, 15:3:109–113 (1997).

K. Panneerselvam, et al. Human Fibroblasts Prefer Mannose Over Glucose as a Source of Mannose for N–Glycosylation, J. Biol. Chem., 272 (37), 23123–23129 (1997).

L. Xie, et al. Integrated Approaches to the Design of Media and Feeding Strategies for Fed–batch Cultures of Animal Cells, Trends in Biotech., 15(3), 109–113 (1997).

J. Ljunggren, Catabolic Control of Hybridoma Cells by Glucose and Glutamine Limited Fed Batch Cultures, Biotechnol. Bioeng., 44(7), 808–818 (1994).

K. Yoda, Time Course of Glutamine a Culture Medium during High–density culture of Mouse C127 Transformants, Annal. of the New York Acad. of Sci., 750, 175–179 (1995).

* cited by examiner

Primary Examiner—Leon B. Lankford, Jr.
Assistant Examiner—Ruth Davis
(74) Attorney, Agent, or Firm—Fulbright & Jaworski L.L.P.

(57) ABSTRACT

The invention concerns a process for the production of a polypeptide with suitable glycosylation by culturing eukaryotic cells and isolating the polypeptide from the culture medium or/and the cells. In this process the desired glycosylated polypeptide can be produced recombinantly with the aid of endogenous gene activation or be produced naturally by the cells.

11 Claims, 1 Drawing Sheet

METHOD FOR PREPARING POLYPEPTIDES WITH APPROPRIATE GLYCOSILATION

Figure 1:
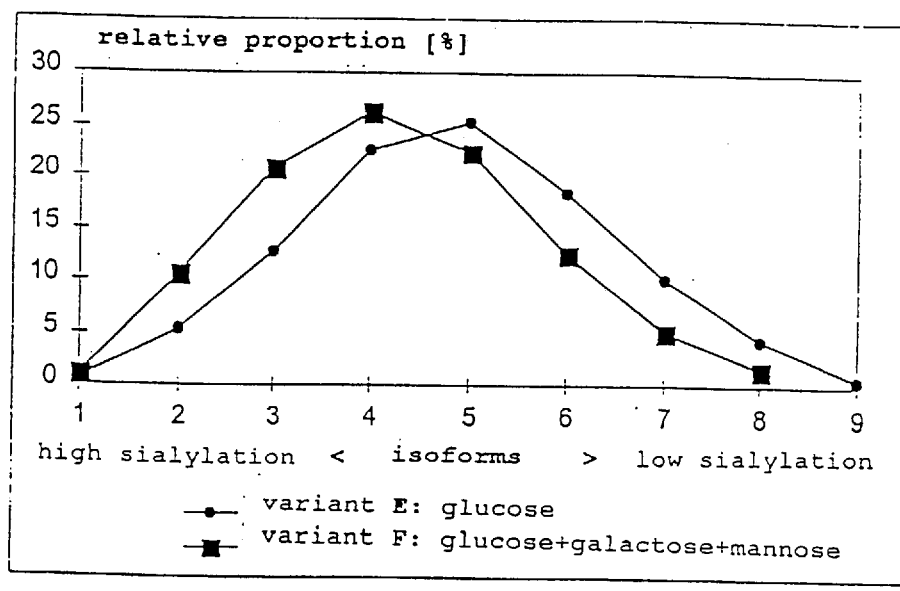

The invention concerns a process for the production of a polypeptide with suitable glycosylation by culturing eukaryotic cells and isolating the polypeptide from the culture medium or/and the cells. In this process the desired glycosylated polypeptide can be produced recombinantly with the aid of endogenous gene activation or be produced naturally by the cells.

The production of glycoproteins by culturing eukaryotic cells is generally carried out in commercial culture media. The addition of certain substrates to the culture medium may be necessary in order to achieve a desired glycosylation of the polypeptide. This is described in the Japanese laid-open patent document H6-292 592 for a batch process in small volumes (<1000 ml), a low initial cell density ($5 \times 10^4$ cells/ml) and a short culture period (48 h) with a human IgM antibody as an example. In this case another sugar such as fructose, mannose, galactose, N-acetylglucosamine, ribose, fucose, N-acetylgalactosamine etc. is used instead of the conventional glucose for the recombinant production of antibodies in mammalian cells e.g. CHO cells. In addition a multi-step culture process is disclosed in which the cells are firstly cultured in a medium containing glucose which is subsequently substituted by a medium containing another sugar.

However, the process described in the Japanese laid-open patent document H6-29592 has serious disadvantages. The concentration of the sugar in the culture medium changes continuously as a result of its consumption during the cell culture so that a constant high degree of glycosylation of the polypeptides is not guaranteed. Furthermore the batch process is unsuitable if a constant substrate concentration is necessary for a desired glycosylation since the initial concentrations of the substrates continuously decrease due to cell metabolism. Moreover the high sugar concentrations required for high cell densities and a constant high degree of glycosylation must already be provided at the start of the fermentation which would, however, inhibit the growth of the cells and hence limit the attainable cell density. Therefore an economical production of highly glycosylated polypeptides is not possible using the process described in the above-mentioned Japanese laid-open patent document.

The culture of eukaryotic cells by a batch process with feeding (fed-batch) in which nutrient solution is added during the culture is known. In this type of process it is possible to achieve a high cell density and a longer culture period by suitable feeding. An example is the continuous and limited feeding of the essential amino acid glutamine which leads to an improved cell growth (Ljunggren et al., Biotech. Lett. 12 (1990), 705–710). The aim of feeding glutamine is to reduce the formation of ammonium since ammonium is toxic for animal cells (Mirabet et al., Biotechnol. Bioeng. 56 (1997), 530–537).

Gawlitzek et al. (Biotechnol. Bioeng. 57 (1998), 518–528) describe that increased concentrations of ammonium ions or glucosamine in the medium of cultured eukaryotic BHK-21 cells lead to an increase of the complexity of N-linked carbohydrate structures in recombinant glycoproteins which are secreted by the cultured cells. However, this finding is inconsistent with the results of Borys et al. (Biotechnol. Bioeng. 43 (1994), 505–514) or Andersen and Goochee (Biotechnol. Bioeng. 47 (1995), 95–105) where an inhibition of glycosylation by elevated ammonium concentrations in the culture medium was found. Hence it becomes clear that the control of ammonium formation in the culture is only an isolated aspect and is therefore not sufficient for the economical production of proteins with suitable glycosylation.

The degree of glycosylation of polypeptides can greatly influence their biological activity. This is elucidated in the following erythropoietin (EPO) example. EPO is a human glycoprotein which stimulates the production of red blood cells. EPO only occurs in the blood plasma of healthy persons in very low concentrations so that it is not possible to provide larger amounts in this manner. EP-B-0 148 605 and EP-B-0 205 564 describe the production of recombinant human EPO in CHO cells. The EPO described in EP-B-0 148 605 has a higher molecular weight than urinary EPO and no O-glycosylation. The EPO described in EP-B-0 205 564 from CHO cells is now available in large amounts and in a pure form.

Furthermore the isolation of human EPO from the urine of patients with aplastic anaemia is known (Miyake et al., J. Biol. Chem. 252 (1977), 5558–5564).

Recombinant and urinary EPO are isolated as a mixture of various isoforms which are known to differ in their degree of sialylation. These EPO isoforms have different isoelectric points and can be separated by isoelectric focussing or capillary electrophoresis (see Tsao et al., Biotech. Bioeng. 40 (1992), 1190–1196; Nieto et al., Anal. Commun. 33 (1996), 425–427; Tran et al., J. Chromatogr. 542 (1991), 459–471; Bietot et al., J. Chromatogr. 759 (1997), 177–184; Watson et al., Anal. Biochem. 210 (1993), 389–393). The isoforms with the highest number of sialic acids have the highest specific activity, whereas those with the lowest number have the lowest activity (see e.g. Imai et al., Eur. J. Biochem. 194 (1990), 457–462; EP-A-0 428 267).

Takeuchi et al., (Proc. Natl. Acad. Sci. USA 86 (1989), 7819–7822) describe a relationship between the biological activity and the sialic acid content and the ratio of biantennary and tetraantennary carbohydrate structures. Takeuchi et al., additionally conclude that the N-acetyl-lactosamine disaccharide units present in the EPO carbohydrate structures do not correlate with the biological activity.

Fukuda et al., (Blood 73 (1989), 84–89) deal with the rate of elimination of EPO from the blood circulation which makes an important contribution to the biological activity and conclude that EPO with a relatively large number of N-acetyl-lactosamine units is more rapidly removed from the circulation than EPO without lactosamine units. Morimoto et al., (Glycoconjugate J. 13 (1996), 1093–1120) describe the separation of EPO isoforms by means of mono-Q chromatography so that the individual fractions are then only composed of a few isoforms. The investigations carried out on these fractions show an equidistribution of all structures in all fractions. No correlation was found between the content of biantennary or triantennary structures or the content of N-acetyl-lactosamine units and the specific activity.

Thus the said prior art shows that there is a general correlation of the biological activity with the sugar structure especially with regard to the content of sialic acids.

Surprisingly it was found that a continuous feeding according to requirements of carbohydrate-containing substrates during a high cell density fermentation or/and use of a mixture of at least 2 carbohydrates during culture enables a high yield of desired protein, such as EPO, with a high degree of glycosylation to be obtained.

Hence a first aspect of the invention concerns a process for isolating a glycosylated polypeptide from eukaryotic cells, wherein the eukaryotic cells are cultured in a suitable medium and the desired polypeptide is isolated from the cells or/and the culture supernatant wherein the process is characterized in that a mixture of at least 2 and preferably at least 3 carbohydrates is added to the culture medium.

The carbohydrates are preferably selected from monosaccharides and disaccharides such as glucose, glucosamine, ribose, fructose, galactose, mannose, sucrose, lactose, mannose-1-phosphate, mannose-1-sulfate and mannose-6-sulfate. Nutrient media are for example suitable which contain glucose or/and mannose or/and galactose. Particularly good results were obtained with nutrient media which contain a mixture of glucose, galactose and mannose for example in a mass ratio of 1:(0.5–3):(1–5) and in particular of 1:(0.7–2.4):(1.8–4.0) where each of the carbohydrates is particularly preferably used in the D(+) form. The total concentration of all sugars during the fermentation is preferably in a range of 0.1 to 10 g/l, particularly preferably in a range of 2 to 6 g/l in the culture medium. The carbohydrate mixture is preferably added dependent on the respective requirement of the cells as elucidated in more detail in the following.

A second aspect of the invention is a process for isolating a glycosylated polypeptide from eukaryotic cells in which the eukaryotic cells are cultured in a suitable medium and the desired polypeptide is isolated from the cells or/and the culture supernatant in which the process is characterized in that nutrients are added in a controlled manner and according to requirements during the culture which comprise at least one essential amino acid for the respective cultured cell line or/and at least one carbohydrate depending on the respective requirement of the cells.

In order to enable a demand-oriented addition of nutrients, the concentration of parameters which correlate with the nutrient requirement of the cells and their consumption rates are determined continuously or at suitable time intervals e.g. at least once daily. In this manner it is possible to quantitatively or/and qualitatively determine the nutrients required for the cell needs and to add them to the culture medium in an appropriate composition and amount. Such parameters can be nutrients or metabolic products of the cells such as the glutamine, the ammonium, the glucose or/and the lactate concentration, in particular the glutamine concentration.

As a result of the controlled and demand-oriented addition of nutrients it is possible to obtain a considerably improved glycosylation even with a high cell density fermentation (cell density at harvest>10×10$^5$ cells/ml and preferably>20×10$^5$ cells/ml) in large fermenters (volume>1 l, e.g. 50 to 10,000 l).

The nutrients added according to this aspect of the invention comprise essential amino acids e.g. glutamine or/and tryptophan or/and carbohydrates and preferably in addition non-essential amino acids, vitamins, trace elements, salts or/and growth factors e.g. insulin. The nutrients preferably include at least one essential amino acid and at least one carbohydrate. These nutrients are preferably metered into the fermentation culture in a dissolved state. The nutrients preferably contain at least glutamine and carbohydrates especially a mixture of at least two carbohydrates as mentioned above. A mixture of glucose, galactose and mannose is particularly preferably used. In addition it is preferred that the nutrients are added according to needs over the entire growth phase of the cells i.e. dependent on the concentration of the selected parameters measured in the culture medium.

The quantity ratio of glutamine to carbohydrates in the nutrient solution is preferably selected such that it essentially corresponds to the consumption ratio in the fermenter. This enables a substantially constant concentration of the individual substrates to be maintained in the fermenter. The concentration of glutamine is preferably maintained at a value which is <150 mg/l in the culture medium and prevents the development of an ammonium concentration of ≧2.3 mmol/l in the culture medium. During the fermentation the total concentration of the sugars is preferably in a range of 0.1 to 10 g/l, particularly preferably in a range of 2 to 6 g/l culture medium as already explained.

The nutrient solution that is used contains a mass ratio of glutamine to sugars which is preferably in a range of 1:3 to 20 and particularly preferably of 1:5 to 15 with reference to the total sugar. When a nutrient solution is used which contains glutamine as well as the three sugars glucose, galactose and mannose, the mass ratio of glutamine to the sugars is preferably 1:(1 to 3):(1 to 5):(2 to 8) and particularly preferably 1:(1.5 to 2.2):(1.5 to 3.6):(4 to 6).

The process according to the invention is fundamentally suitable for the production of any glycosylated polypeptides. However, polypeptides are suitable which carry one or several sialic acid residues since especially the degree of sialylation of the polypeptides can be increased by the process according to the invention. Furthermore it is also possible to influence the antennarity.

The process according to the invention is particularly suitable for the production of polypeptides that can be used therapeutically since their biological activity and hence also their pharmaceutical efficacy depends on the glycosylation and in particular on the degree of sialylation or/and on the antennarity. For example the glycosylated polypeptides can be selected from the group comprising physiologically active glycoproteins such as lymphokines, cytokines, immunoglobulins and hormones e.g. EPO, thrombopoietin (TPO), G-CSF, GM-CSF, interleukins, interferons, blood coagulation factors and tissue plasminogen activators. Polypeptides can be natural human polypeptides or recombinant muteins of such human polypeptides. The glycosylated polypeptide EPO is particularly preferred.

The cells used for the culture can in principle be any eukaryotic cells such as yeast cells or insect cells. However, the eukaryotic cells are preferably mammalian cells e.g. cells derived from the hamster such as CHO or BHK or in particular human cells. Furthermore it is preferred that the eukaryotic cells are continuous cell lines of animal or human origin such as the human cell lines HeLaS3 (Puck et al., J. Exp. Meth. 103 (1956), 273–284), Namalwa (Nadkarni et al., Cancer 23 (1969), 64–79), HT1080 (Rasheed et al., Cancer 33 (1973), 1027–1033) or cell lines derived therefrom. The desired polypeptide can be produced in the cultured cells (a) by expression of a natural endogenous gene, (b) by expression of an activated endogenous gene or/and (c) by expression of an exogenous gene (recombinantly).

Cells are particularly preferred in which the desired polypeptide is produced by expression of an endogenous gene activated by homologous recombination e.g. the cell lines disclosed in the European Patent application EP 97 112 640.4 which are able to produce large amounts of EPO.

The cells can be cultured basically in any desired manner. However, culture as a suspension is preferred. Furthermore it is preferred that the cells are cultured in a medium containing a low serum content e.g. a maximum of 1% (v/v) or in particular in a serum-free medium e.g. in a serum-free, low-protein fermentation medium (cf. e.g. WO 96/35718). Examples of suitable culture media are basal media such as e.g. RPMI 1640, DMEM, F12 or eRDF containing appropriate additives. The process according to the invention allows a culture in large fermenters i.e. in a culture volume of more than 1 l, preferably more than 10 l, for example 50 l to 10,000 l. Furthermore the process according to the invention allows a high cell density fermentation which means that the concentration of the cells after the growth phase (i.e. at the time of harvest) is more than $10 \times 10^5$ cells/ml and particularly preferably more than $20 \times 10^5$ cells/ml.

The culture is preferably carried out as a repeated batch process with feeding according to requirements in which a portion of the culture broth is harvested after a growth phase and the remainder of the culture broth remains in the fermenter which is subsequently again filled up with fresh medium to the working volume. The process according to the invention enables the desired glycosylated polypeptide to be harvested in very high yields. Hence the concentration at the time of harvest is for example at least 30 mg and in particular at least 40 mg of the desired polypeptide per 1 culture medium.

Yet a further aspect of the invention is a process for isolating a glycosylated polypeptide from eukaryotic cells in which the eukaryotic cells are cultured in a suitable medium and the desired polypeptide is isolated from the cells or/and the culture supernatant, the process being characterized in that the culture is carried out at a temperature of $\leq 35.5°$ C., preferably between 33 and 35.0° C. It was surprisingly found that the proportion of polypeptides with the desired glycosylation can be considerably increased by lowering the temperature during the culture.

The invention is further elucidated by the following figures and examples with regard to the production of EPO in HeLa S3 cells.

Figure 2:
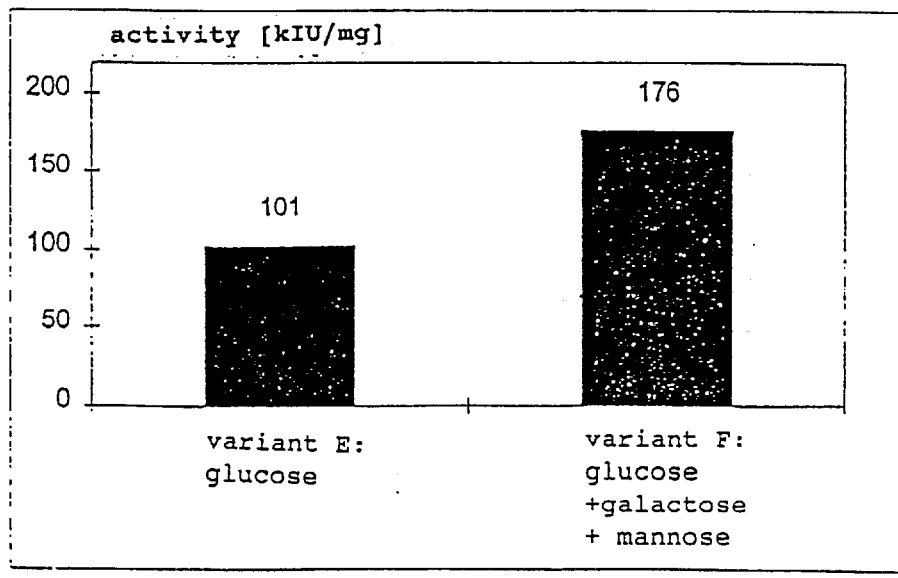

FIG. 1: shows the dependence of the relative proportion of individual EPO isoforms on the carbohydrates added to the culture medium and FIG. 2: shows the dependence of the biological activity of EPO preparations on the carbohydrates added to the culture medium.

EXAMPLES

Example 1

Determination of the Specific Activity of EPO In Vivo

Important factors for the in vivo biological activity of EPO are the degree of glycosylation e.g. the number of tetraantennary structures relative to the total number of carbohydrate chains, the number of N-acetyl lactosamine units with reference to one glycosylation site of the EPO molecule and the sialic acid content per EPO molecule. Up to 14 isoforms occur corresponding to the number of terminally-bound sialic acids which can be separated on the basis of their charge e.g. with capillary zone electrophoresis (CZE). The most acidic highly sialylated isoforms 1 to 5 are decisive for the biological in vivo activity of EPO.

The dose-dependent activity of EPO on the multiplication and differentiation of erythrocyte precursor cells was determined in vivo in mice by means of the increase in reticulocytes in the blood after EPO administration.

For this various doses of the EPO sample to be analysed and of an EPO standard (standardized with the EPO WHO standard) were each administered parenterally to eight mice. The mice were subsequently kept under constant defined conditions. Blood was collected from the mice 4 days after EPO administration and the reticulocytes were stained with acridine-orange. The reticulocyte count per 30,000 erythrocytes was determined by microfluorimetry in a flow cytometer by analysing the red-fluorescence histogram.

The biological activity was calculated from the values for the reticulocyte counts of the sample and of the standard at different doses according to the method described by Linder of pairwise determination of concentration with parallel straight lines (Linder, "Planen und Auswerten von Versuchen", 3rd. edition, 1969, Birkenhäuser Verlag, Basel).

Example 2

Determination of the Content of Sialic Acid Residues

The sialic acid content was determined chromatographically by means of HPAEC-PAD (high pH anion exchange chromatography with pulsed amperometric detection) and a Dionex system after enzymatic cleavage of the sialic acids with neuraminidase from *Arthrobacter ureafaciens* (*A. ureaf.*, Boehringer Mannheim).

Preparations each containing 22 μg EPO from various preparations of CHO and human cell lines (e.g. HeLa S3) were adjusted to an EPO concentration of 0.2 mg/ml in 5 mM Na phosphate buffer, pH 7.2. Half of each preparation was used to exactly determine the EPO amount by means of RP-HPLC. 5 mM U neuraminidase from *A. ureaf.* was added to the second half of the preparations and incubated overnight (ca. 18 h) at 37° C. Subsequently the digestion mixtures were halved, diluted 20-fold to 500 μl with $H_2O$ and 50 μl thereof (corresponds to ca. 27 pmol EPO) was applied to the Dionex system. The following chromatographic parameters were used for this:

| column: | CarboPac PA 100 |
| --- | --- |
| flow: | 1.0 ml/min |
| detector sensitivity: | 300 nA |

| gradient: | t (min) | % buffer B |
| --- | --- | --- |
| | 0 | 17 |
| | 7 | 17 |
| | 9 | 100 |
| | 12 | 100 |
| | 13 | 0 |
| | 20 | 0 |

| buffer A: | 0.1 M NaOH |
| --- | --- |
| buffer B: | 0.1 M NaOH; 0.5 M Na acetate |

The amount of sialic acids in the applied sample was determined with the aid of a calibration line which was obtained from values of a sialic acid standard that was also analysed (Boehringer Mannheim). The sialic acid content (mole sialic acid/mole EPO) was calculated from the result of the sialic acid determination (Dionex system) and the determination of the amount of EPO used by means of RP-HPLC.

Example 3

Determination of the Proportions of Biantennary, Triantennary and Tetraantennary Carbohydrate Structures The N-linked carbohydrate structures were analysed chromatographically by HPAEC-PAD on a Dionex system. The asialo oligosaccharides of EPO preparations from CHO and human cell lines (e.g. HeLa S3) were isolated by enzymatic cleavage with N-glycosidase F (Boehringer Mannheim) and neuraminidase from *A. ureaf.* (Boehringer Mannheim).

Ca. 30 μg EPO per mixture was desalted by means of MicroCon ultracentrifugation units (Amicon, exclusion size 10 kD) and adjusted with 10 mM Na phosphate buffer, pH 7.2 to a concentration of 0.3 mg/ml. Subsequently 1 U N-glycosidase F and 10 mU neuraminidase was added to each mixture and incubated overnight (ca. 18 h) at 37° C. In order to separate the EPO polypeptide moiety from the cleaved oligosaccharides, the mixtures were centrifuged through Ultrafree centrifugation units (Millipore, exclusion size 10 kD) after incubation and the Ultrafree device was washed again twice with 20 μl $H_2O$. The oligosaccharides contained in the filtrate were made up to 150 μl with $H_2O$ and 100 μl thereof was analysed on the Dionex system. The following chromatographic parameters were used for this:

| column: | CarboPac PA 100 | |
|---|---|---|
| flow: | 1.0 ml/min | |
| detector sensitivity: | 300 nA | |
| gradient: | t (min) | % buffer B |
| | 0 | 0 |
| | 2 | 0 |
| | 60 | 10 |
| | 62 | 100 |
| | 67 | 100 |
| | 69 | 0 |
| | 80 | 0 |
| buffer A: | 0.1 M NaOH | |
| buffer B: | 0.1 M NaOH; 0.5 M Na acetate | |

The peaks were identified in a chromatogram of N-sugars of the complex type by standard oligosaccharides (Oxford Glyco Systems) and verified by enzymatic digestion of the oligosaccchharides of EPO with the enzyme endo-β-galactosidase or fucosidase and subsequent analysis on the Dionex system. The percentages of biantennary, triantennary and tetraantennary structures were calculated by means of the areas of the peaks that represent the corresponding N-sugar structure relative to the total peak area (sum of the peak areas of biantennary, triantennary and tetraantennary structures).

Example 4

Determination of the Content of N-Acetyl-lactosamine Units and the Average Content of Additional N-Acetyl-lactosamine Units (Repeats)

The total number of N-acetyl-lactosamine units in the N-linked carbohydrate structures of EPO (i.e. in the core carbohydrate structures) was calculated from the peak areas of the chromatograms of the experiments of example 3.

The number of the average content (n) of N-acetyl-lactosamine units per carbohydrate chain was calculated as follows:

$n = \Sigma\% (bi) \times 2 + \% (tri) \times 3 + \% (tetra) \times 4 + \% (tri+1r) \times 4 + \% (tetra+1r) \times 5 + \% (tri+2r) \times 5 + \% (tetra+2r) \times 6$ in which

| % (bi) = | percentage of biantennary structures relative to the total number of carbohydrate chains |
|---|---|
| % (tri) = | percentage of triantennary structures without additional N-acetyl-lactosamine units |
| % (tetra) = | percentage of tetraantennary structures without additional N-acetyl-lactosamine units |
| % (tri + 1r) = | percentage of triantennary structures with 1 additional N-acetyl-lactosamine unit |
| % (tetra + 1r) = | percentage tetraantennary structures with 1 additional N-acetyl-lactosamine unit |
| % (tri + 2r) = | percentage of triantennary structures with 2 additional N-acetyl-lactosamine units |
| % (tetra + 2r) = | percentage of tetraantennary structures with 2 additional N-acetyl-lactosamine units |

A further important parameter is the amount of N-acetyl-lactosamine units which can be bound to the core carbohydrate structures as so-called repeats. The repeat content is specified as the percentage of repeat-containing carbohydrate structures relative to the totality of carbohydrate structures (bi+tri+tetra=100%) This proportion of repeats can be different in EPO preparations from CHO cells and from human cells.

Example 5

Influencing the Biological Activity of EPO by Controlled Feeding According to Requirements Cultures were carried out as repeated batch processes with feeding as required (repeated fed batch) at a temperature of 36.5° C. For this serum-free, protein-poor culture medium was placed in a stirred fermenter (total working volume: 10 L) and inoculated once with an inoculum culture. The cell density after inoculation was in the range of $3\pm1\times10^5$ living cells/ml.

After a growth phase of 144±24 hours, a portion of the culture broth was harvested. The remainder of the culture broth remained in the fermenter and represented the inoculum for the next growth phase; for this purpose the fermenter was again filled up with fresh medium to the working volume.

The culture supernatant containing EPO was obtained by centrifuging the fermentation culture.

Nutrient solution was continuously supplied to the culture during the growth phase. For this purpose a storage vessel containing nutrient solution was coupled to the fermenter. The nutrient solution contained amino acids, vitamins, insulin, trace elements, salts, glutamine and carbohydrates. Two fermentations were carried out as follows:

In fermentation A the nutrient solution contained D-(+)-glucose as the sugar and in fermentation B the sugars were D-(+)-glucose, D-(+)-galactose and D-(+)-mannose. The mass ratio of glutamine to the sugars was 1:2.2:3.6:6 in fermentation B. The concentration of the individual sugars in the nutrient solution was between 7.2 and 18 g/l.

The glutamine concentration in the culture was periodically analysed in fermentation B and the consumption was calculated. The momentary volume flow of the nutrient solution was matched to the requirement of the cells for nutrients. In fermentation A the glutamine concentration was not used as a controlled variable. The nutrient solution in fermentation B contained a mixture of the sugars D-(+) glucose, D-(+)galactose and D-(+)mannose in a mass ratio of 2:3:5. The concentration of all sugars in the fermenter was kept in the range 2 to 6 g/l during the culture by corresponding feeding.

The cell density changed during the growth to more than $20\times10^5$ cells/ml, typically $30\pm10\times10^5$ cells/ml at the time of harvest. At the time of harvest the concentration of EPO was typically 40±10 mg/l.

The concentration of human erythropoietin was determined, for example by ELISA, in the harvested culture broths. A percentage distribution of the isoforms of this protein that occurred was for example determined by separating with capillary zone electrophoresis (CZE).

Table 1 shows a comparison of the distribution of EPO isoforms between a fermentation A fed with a nutrient solution containing glucose and a fermentation B fed with a nutrient solution containing glucose, mannose and galactose in a controlled and requirement-oriented manner. The contents of EPO isoforms in fermentation B were calculated as percentages of the corresponding isoforms of fermentation A. The latter were each standardized to 100%. The data show that the desired higher glycosylated EPO isoforms 2–4 are present in a substantially higher proportion during the fermentation compared with fermentation A.

TABLE 1

| Isoform name in the CZE | 1 | 2 | 3 | 4 | 5 | 6 | 7 | 8 |
|---|---|---|---|---|---|---|---|---|
| | [%] | [%] | [%] | [%] | [%] | [%] | [%] | [%] |
| Fermentation A: feeding with glucose | n.d. | 100 | 100 | 100 | 100 | 100 | 100 | 100 |
| Fermentation B: feeding with glucose, mannose and galactose as required | n.d. | 136 | 140 | 115 | 102 | 91 | 76 | 55 | n.d. = not determinable, since the value is below the detection limit

The isoform pattern obtained with feeding was reproducible in four successive harvests from a fermentation with controlled and demand-oriented feeding of the nutrient solution.

Example 6

Influencing the Biological Activity of EPO by Changing the Culture Temperature

The procedure was as described in example 5 (fermentation B) in a fed-splitbatch process with controlled and demand-oriented feeding except that the fermenter temperature was 35.0° C. instead of 36.5° C. and the fermentation was carried out on a 1000 l scale.

Table 2 shows a comparison of the EPO isoform distribution between a fermentation C at 36.5° C. and a fermentation D at 35.0° C. each with controlled feeding of a nutrient solution. The contents of EPO isoforms in fermentation D were calculated as percentages of the corresponding isoforms of fermentation C. The latter were each standardized to 100%. The data show that the acidic EPO isoforms 2 to 4 can be considerably increased by decreasing the temperature.

TABLE 2

| Isoform name in the CZE | 1 | 2 | 3 | 4 | 5 | 6 | 7 | 8 |
|---|---|---|---|---|---|---|---|---|
| Relative isoform distribution | [%] | [%] | [%] | [%] | [%] | [%] | [%] | [%] |
| Fermentation C: temperature 36.5° C. | n.d. | 100 | 100 | 100 | 100 | 100 | 100 | 100 |
| Fermentation D: temperature 35.0° C. | n.d. | 131 | 116 | 110 | 94 | 100 | 88 | 86 | n.d. = not determinable, since the value is below the detection limit

Example 7

Influencing the Biological Activity of EPO by Changing the Carbohydrate Composition in the Medium The process presented in the following shows that it is possible to change the quality of human erythropoietin by changing the carbohydrate supply in the feeding medium.

Two variants of the process described above are shown (called fermentation E and fermentation F in the following) which differ in the composition of the media used.

In both preparations the formulation of the culture medium is based on modified eRDF medium. No serum was used but rather recombinant insulin (only protein additive) and further supplements (e.g. selenite, putrescine, hydrocortisone, iron sulfate) which are usually used in serum-free or protein-free media.

The feed nutrient solution is also based on modified eRDF medium but does not contain the salts KCl, $Na_2HPO_4$ and NaCl.

The major difference between fermentations E and F is the addition of various monosaccharides to the feed medium.

Fermentation E:

The usual sugar D-(+)-glucose was used for fermentation E. The initial concentration was 3 g/l. By appropriately feeding the glucose-containing nutrient solution, the glucose concentration in the culture broth was maintained at 3±0.5 g/l during the entire culture.

The culture period was typically 100±20 h. The concentration of EPO was typically 40±10 mg/l at the time of harvest.

Fermentation F:

In addition to D-(+)-glucose, the sugars D-(+)-galactose and D-(+)-mannose were added in a mass ratio of ca. 1:2:3 to the feed medium for fermentation F. During the culture the concentration of all sugars was kept in a range between 0.25 g/l and 3.5 g/l by appropriate feeding.

The culture period was typically 100±20 hours. The concentration of EPO at the time of harvest was typically 40±10 mg/l.

Erythropoietin was purified from the culture supernatants. The purification procedure was designed such that the distribution of relevant isoforms of the glycoprotein was not influenced.

The isoform distribution of the purified erythropoietin was determined as described above. The carbohydrate structures of the isoforms of human erythropoietin and their distribution in the harvested culture supernatants was different in fermentation E and fermentation F. Fermentation F has a considerably higher proportion of isoforms 2, 3 and 4 compared to fermentation E. These differences are caused by feeding the monosaccharides mannose and galactose (cf. FIG. 1).

The biological activity determined by the normo mouse test (example 1) correlates with the distribution and the carbohydrate structures of the EPO isoforms (FIG. 2). The carbohydrate structures of the EPO preparations obtained from the culture supernatants E and F were examined with CZE and HPAEC analysis.

The antennarity (content of bistructures, tristructures and tetrastructures), the content of N-acetyl-lactosamine units (LE), the sialic acid content (SA) and the product of LE and SA of the two epo preparations are shown in Table 3.

TABLE 3

|  | bi [%] | tri [%] | tetra [%] | SA content | LE content | LE × SA |
|---|---|---|---|---|---|---|
| Fermentation E | 12.6 | 25.4 | 62.0 | 10.8 | 10.8 | 116.7 |
| Fermentation F | 10.1 | 19.2 | 70.6 | 11.6 | 11.25 | 130.5 |

What is claimed is:

1. A process for increasing the glycosylation of a polypeptide when producing glycosylated polypeptides in mammalian or insect cells while maintaining cell specific productivity comprising:
   (a) culturing mammalian or insect cells in a culture medium;
   (b) monitoring the concentration of at least one parameter selected from nutrients and metabolites of the cultured cells wherein said parameter correlates to the nutrient requirement of the cells and determining the consumption rate of said parameter;
   (c) adding a mixture of at least two carbohydrates to the culture medium in an amount sufficient to meet the nutrient requirements of the cells to maintain cell specific productivity, wherein said amount is based on the consumption rate of the parameter in step (b); and
   (d) isolating the glycosylated polypeptide from the culture medium,
   wherein culturing the cells under the condition (a)–(c) increases the glycosylation of the polypeptide while maintaining cell specific productivity.

2. The process of claim 1, wherein the carbohydrate mixture comprises glucose, mannose and/or galactose.

3. The process of claim 1, wherein the carbohydrate mixture is added to the medium at concentrations to maintain an essentially constant concentration of said carbohydrates.

4. A process for increasing the glycosylation of a polypeptide when producing glycosylated polypeptides in mammalian or insect cells while maintaining cell specific productivity comprising:
   (a) culturing mammalian or insect cells in a culture medium;
   (b) monitoring the concentration of at least one parameter selected from nutrients and metabolites wherein said parameter correlates with the nutrient requirements of the cells and determining the consumption rate of said parameter;
   (c) adding a nutrient mixture comprising at least one essential amino acid and/or at least one carbohydrate to the medium in an appropriate amount sufficient to meet the nutrient requirements of the cells, wherein such amount is based on the consumption rate of the parameter in step (b); and
   (d) isolating the glycosylated polypeptide from the culture medium,
   wherein culturing the cells under the conditions (a)–(c) increases the glycosylation of the potypeptide while maintaining cell specific productivity.

5. The process of claim 4, wherein glutamine concentration is assayed to determine the nutrient requirements of the cells.

6. The process of claim 4, wherein the nutrient mixture further comprises non-essential amino acids, vitamins, trace elements, growth factors or mixtures thereof.

7. The process of claim 4, wherein the nutrient mixture comprises at least two carbohydrates.

8. The process of claim 1, wherein the glycosylated polypeptide is erythropoietin.

9. The process of claim 1, wherein the cells are cultured at a temperature of $\leq 35.5°$ C.

10. The process of claim 4, wherein the glycosylated polypeptide is erythropoietin.

11. The process of claim 4, wherein the cells are cultured at a temperature of $\leq 35.5°$ C.

* * * * *